(12) United States Patent  
Pescatore et al.

(10) Patent No.: US 8,326,403 B2
(45) Date of Patent: Dec. 4, 2012

(54) METHOD AND APPARATUS FOR DETERMINING MOVEMENT OF AN OBJECT IN AN IMAGER

(75) Inventors: Jérémie Pescatore, Le Chesnay (FR); Benoit Le Ny, La Verenne (FR); Sébastien Gorges, Nancy (FR); Marie-Odile Berger, Maron (FR)

(73) Assignee: General Electric Company, Schenectady, NY (US)

( * ) Notice: Subject to any disclaimer, the term of this patent is extended or adjusted under 35 U.S.C. 154(b) by 1035 days.

(21) Appl. No.: 11/355,733

(22) Filed: Feb. 16, 2006

(65) Prior Publication Data
US 2007/0238947 A1 Oct. 11, 2007

(30) Foreign Application Priority Data
Feb. 21, 2005 (FR) ...................................... 05 01741

(51) Int. Cl.
*A61B 5/05* (2006.01)
(52) U.S. Cl. ........................................ 600/426; 378/205
(58) Field of Classification Search .................. 600/426, 600/407, 424, 427; 378/205, 20
See application file for complete search history.

(56) References Cited

U.S. PATENT DOCUMENTS

| | | | | |
|---|---|---|---|---|
| 5,442,674 A | * | 8/1995 | Picard et al. ..................... | 378/20 |
| 5,712,895 A | * | 1/1998 | Negrelli et al. ................ | 378/207 |
| 6,206,566 B1 | * | 3/2001 | Schuetz ......................... | 378/205 |
| 6,359,960 B1 | * | 3/2002 | Wahl et al. ...................... | 378/20 |
| 6,405,072 B1 | * | 6/2002 | Cosman ......................... | 600/426 |
| 6,491,430 B1 | * | 12/2002 | Seissler ......................... | 378/207 |
| 6,738,656 B1 | * | 5/2004 | Ferre et al. .................... | 600/426 |
| 6,851,855 B2 | * | 2/2005 | Mitschke et al. ............. | 378/207 |
| 7,186,023 B2 | | 3/2007 | Morita et al. | |

FOREIGN PATENT DOCUMENTS

JP 2005021675 A 1/2005
WO 00/54689 A1 9/2000

OTHER PUBLICATIONS

Veress et al., "Patellar Tracking Patterns Measurement by Analytical X-Ray Photogrammetry", J. Biomechanics, vol. 12, No. 9, Jan. 1979, pp. 639-650.
Kaptein et al., "A new type of model-based Roentgen stereophotogrammetric analysis for solving the occluded marker problem." J. of Biomechanics, vol. 38, Nov. 2005, pp. 2330-2334.
Simon et al. "Real time registration of known or recovered multi-planar structures: application to AR", BMVC 2002.
Unofficial Translation of JPO Offiicial Action from corresponding JP Application No. 2006-037489, May 11, 2011.

* cited by examiner

*Primary Examiner* — Tse Chen
*Assistant Examiner* — Rochelle Reardon
(74) *Attorney, Agent, or Firm* — Global Patent Operation

(57) ABSTRACT

A method and apparatus for determining the three-dimensional movement of a patient positioned on a table between an X-ray source and an image receiver of an X-ray imaging apparatus is presented. The apparatus has an X-ray source positioned opposite an image receiver, the X-ray source and the image receiver being driven in rotation about an axis. The method and apparatus has the following operation: radio-opaque markers are placed on the patient's body; at least one first radiographic image of the patient is taken for a first determined fixed position of the imaging apparatus; at least one second radiographic image of the patient is taken for a second determined fixed position; and a matrix of the three-dimensional movement of the patient is determined on the basis of the two-dimensional movements of the markers in the radiographic images, the X-ray source constituting a fixed reference frame.

6 Claims, 3 Drawing Sheets

METHOD AND APPARATUS FOR DETERMINING MOVEMENT OF AN OBJECT IN AN IMAGER

CROSS-REFERENCE TO RELATED APPLICATIONS

This application claims the benefit of a priority under 35 USC 119 (a)-(d) to French Patent Application No. 05 01741 filed Feb. 21, 2005, the entire contents of which are hereby incorporated by reference.

BACKGROUND OF THE INVENTION

An embodiment of the present invention relates to a method and apparatus for determining the movement of an object in an imager. In particular, an embodiment of the present invention relates to three-dimensional movement of a patient positioned on a table between a radiation source and an image receiver of an imaging apparatus.

In the field of medical imaging, it is well known to use radio-opaque markers positioned on the object, such as a patient, as reference points in order to assist the guiding of surgical instruments during an operation and/or to permit the merging of images, for instance the superposition of images acquired by an imaging apparatus. The imaging apparatus conventionally comprises a means for providing a radiation source, such as X-rays, positioned opposite a means for receiving an image, the means for providing a radiation source and the means for receiving an image being driven in relative rotation about at least one axis, usually three axes, means for operating, means for acquisition, means for visualizing the images and means for control. The patient is positioned on a table that can be moved in the three possible translations associated with a given space, i.e., longitudinally, laterally and vertically, so that the part of the patient's body to be examined and/or treated extends between the means for providing a radiation source and the means for receiving an image. This mobility of the table and the radiation source and the image receiver allows a practitioner to acquire images for any part of the body of a patient lying on the table. For instance, it is customary to use two-dimensional fluoroscopic images obtained by irradiating the patient with low X-ray doses during an intervention in order to guide the instrument in the patient's organ to be treated. The information associated with these fluoroscopic images may preferably be introduced into three-dimensionally reconstructed images in order to improve the guiding of the surgical instruments. Alternatively, acquired three-dimensional images may be projected onto the two-dimensional fluoroscopic images acquired during the intervention.

In order to permit these projections of 3D images onto 2D fluoroscopic images or, conversely, to reposition the 2D fluoroscopic image information in 3D images, it is necessary to determine the acquisition parameters of the 2D fluoroscopic images placed on the patient's body region to be examined. This is the case, for example, in U.S. Pat. No. 6,359,960 that describes a method for automatically determining the three-dimensional coordinates of markers without the intervention of a user. The method comprises detecting the positions of the markers in two-dimensional projections then, by an inverse projection, in determining the coordinates of the markers identified in three dimensions, the geometry of the projections being known.

These methods for determining the three-dimensional coordinates of markers positioned on the patient make it possible to guide surgical instruments during an operation and/or to allow merging of images, for instance projection of 3D images into 2D radiographic images or vice versa; These methods nevertheless assume that the patient remains perfectly stationary when the three-dimensional coordinates of the markers are being determined. It is very common for the patient to move during the procedure, however, leading to inaccuracy in the projections of the 3D images into the radiographic images, or vice versa, which may lead to an interpretation error of the visualized images.

BRIEF DESCRIPTION OF THE INVENTION

An embodiment of the invention overcomes this drawback by providing a method and apparatus for determining the three-dimensional movement of a patient positioned on a table between an X-ray source and an image receiver of an X-ray imaging device, in order to adjust the projection of a three-dimensionally image of the patient's body onto radiographic images and/or to reposition two-dimensional fluoroscopic image information in three-dimensionally reconstructed images displayed on the means for visualization of the imaging apparatus.

An embodiment of the invention relates to a method and apparatus for determining the three-dimensional movement of an object positioned on means for support between a means for providing a radiation source and means for receiving an image, the means for providing a radiation source positioned opposite the means for receiving an image, the means for providing a radiation source and the means for receiving an image being driven in relative in rotation about at least one axis, means for operating, means for acquisition, means for visualizing the images and means for control.

An embodiment of the method and apparatus relates to the determination of the three-dimensional movement of an object positioned on a means for support between a means for providing a radiation source and a means for receiving an image in an imaging apparatus. The method and apparatus in particular relates to placing a plurality of markers, at least three radio-opaque markers, on a body of the object, the markers constituting a fixed reference frame. Taking or acquiring at least one first radiographic image of the object for a first determined fixed position of the imaging apparatus in the reference frame of the markers. Taking or acquiring at least one second radiographic image of the object for a second determined fixed position of the imaging apparatus in the reference frame of the markers. Determining a matrix of the three-dimensional movement of the object with respect to the means for providing a radiation source of the imaging apparatus on the basis of the two-dimensional movements of the markers in the radiographic images, the means for providing a radiation source constituting a fixed reference frame.

BRIEF DESCRIPTION OF THE DRAWINGS

Other advantages and characteristics will be understood more clearly from the following description of several alternative embodiments, given by way of non-limiting examples, of the method on the basis of the appended drawings in which.

DETAILED DESCRIPTION OF THE INVENTION

Figure 1:
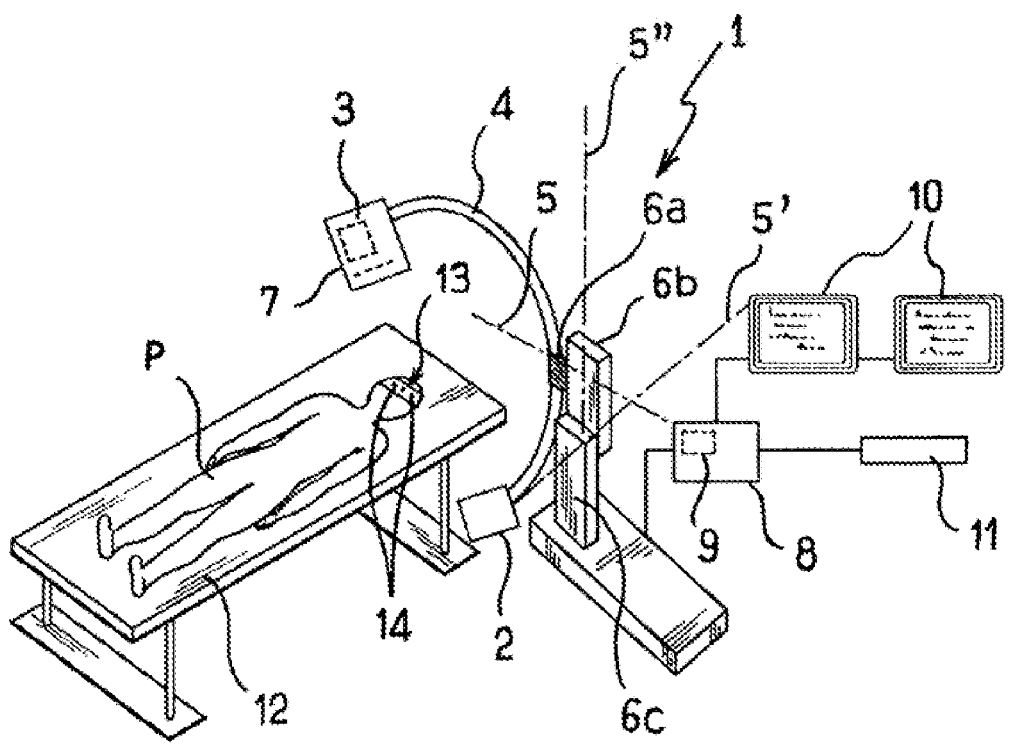
FIG. 1 is a schematic perspective view of an embodiment of an imaging apparatus.

Referring to FIG. 1, an imaging apparatus 1 conventionally comprises means for receiving an image 2 (such as a digital image receiver), means for providing a radiation 3, such as X-ray, emitting radiation onto the means for receiving an image 2, the means for receiving an image 2 and the means for providing a radiation source 3 being respectively positioned at the end of a C-shaped or U-shaped arm 4. Arm 4 pivots about three axes 5, 5' and 5'', which are schematically represented by dots and dashes. The C-shaped arm 4 pivots about an axis 5 secured to a carriage 6a that slides along an intermediate arm 6b. Intermediate arm 6b can pivot about a second axis 5' perpendicular to a face of an L-shaped base 6c, which can pivot about a vertical axis 5'' by means of a rotary linkage. The C-shaped arm 4 can therefore pivot about three axes 5, 5' and 5'', the axes forming a reference system for a specific position of the C-shaped arm 4. A position of the C-shaped arm 4 can thus be expressed in the reference system defined by these three axes 5, 5' and 5'' at a position determined by three angles L, P and C, which the C-shaped arm 4 respectively forms with the axes 5, 5' and 5''. SID will be used to denote the distance separating the means for providing a radiation source 3 from the means for receiving an image 2, the distance SID varying according to the position of the C-shaped arm 4 in view of its mechanical deformation.

The imager apparatus 1 furthermore comprises an adjustable collimator 7 positioned at the exit of the means for providing a radiation source 3. The imaging apparatus 1 also comprises means for operating 8 connected to the means for providing a radiation source 3, to the collimator 7, to the means for receiving an image 2, to means for acquisition 9 and to means for visualization 10. The means for control 11 can be a keyboard, a mouse, control buttons or the like, are connected to the means for operating 8.

Figure 2:
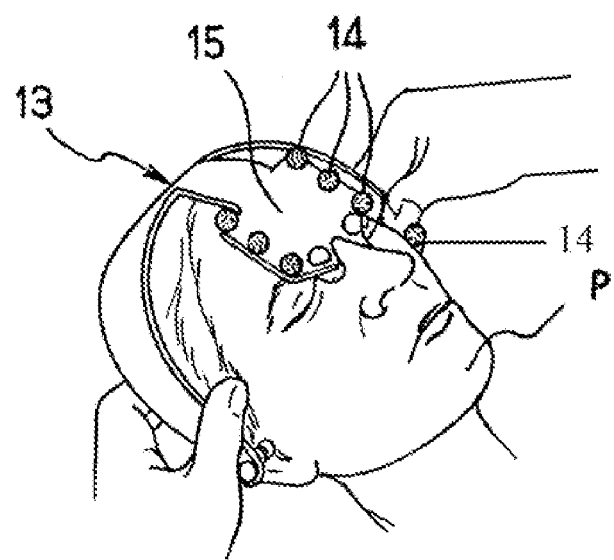
FIG. 2 is a perspective view of the head of a patient wearing a support headpiece carrying radio-opaque markers.
Figure 3:
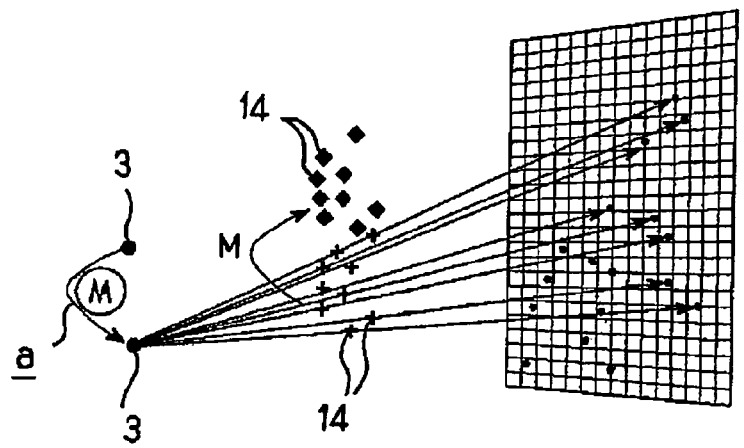
FIG. 3 is a schematic perspective view of the movement of the projections of the markers on an image receiver from a first position to a second position.

An object, such as patient P, is disposed on a means for support 12, such as a table, extending between the means for providing a radiation source 3 and the means for receiving an image 2. In order to determine the three-dimensional movement of the object, the object is fitted with a headpiece 13, as represented in FIG. 2, the headpiece having radio-opaque markers 14. The markers extend in the same plane on a rectangular support 15 extending over the forehead of the patient P. It will be noted that the table 12 can be moved in the three possible translations associated with a given space, i.e., longitudinally, laterally and vertically, so as to allow a practitioner to acquire images for any part of the body of a patient lying on the table 12. At least one first radiographic image of the patient is taken for a first determined fixed position of the imaging device on which the markers 14 appear, without the patient having moved, and a second radiographic image of the patient is taken for a second determined fixed position of the imaging device on which the markers 14 appear, the patient having moved with respect to their position when the first radiographic image was taken. The matrix of the three-dimensional movement of the patient with respect to the radiation source is then determined on the basis of the two-dimensional movements of the markers 14 in the radiographic images, the radiation source constituting a fixed reference frame. The three-dimensional movement M=(R/T) of the markers 14, i.e., of the patient, is equivalent to the inverse movement $M^{-1}$ of the radiation source 3, as represented in FIG. 3, or planes containing the radiographic images if the markers are assumed to be fixed in space. The term movement of the markers 14 is intended to mean a rigid three-dimensional movement, i.e., the distances separating the markers remain unchanged during their movement. Referring to FIG. 3, the movement of the markers 14 from a first position represented by crosses, to a second position where the markers 14 are represented by squares, corresponds to a movement of the radiation source 3 as indicated by the arrow a.

Considering on the one hand $P_1 = I_1 * E_1$, the projection matrix corresponding to the position of the imaging apparatus when the radiographic image is taken in the first position of the imaging apparatus, $I_1$ being the matrix of the intrinsic parameters of the imaging apparatus in its first position and $E_1$ being the matrix of the extrinsic parameters of the imaging apparatus in its first position, where the patient has not moved, and on the other hand $P_2 = I_2 * E_2$, the projection matrix corresponding to the position of the imaging apparatus when the radiographic image is taken in the second position of the imaging apparatus, where the patient has moved with respect to the position when the first radiographic image was acquired, $I_2$ being the matrix of the intrinsic parameters of the imaging apparatus in its second position and $E_2$ being the matrix of the extrinsic parameters of the imaging apparatus in its second position, the movement M can be written in the form $M = (R/T) = E_1^{-1} * E_2$. The movement M of the markers is thus equivalent to the movement of the extrinsic parameters between position 1 and position 2 of the imaging apparatus 1 in the fixed reference frame of the markers 14. In order to determine the patient's movement M, therefore, the matrix of the intrinsic parameters $I_1$ of the imaging apparatus when taking the first radiographic image and the matrix of the intrinsic parameters $I_2$ of the imaging apparatus when taking the second radiographic image are determined, the intrinsic parameters $I_1$ and $I_2$ being determined beforehand by any suitable method, for example a multi-image calibration method, and being equal. The matrix of the extrinsic parameters $E_2$ of the imaging apparatus when taking the second radiographic image is then determined, as a function of the matrix of the intrinsic parameters $I_1$ of the imaging apparatus when taking the first radiographic image. The inverse matrix of the extrinsic parameters $E_1^{-1}$ of the imaging apparatus is subsequently determined on the basis of the intrinsic parameters $I_1$, then the matrix M corresponding to the patient's three-dimensional movement is determined as a function of the inverse matrix $E_1^{-1}$ of the extrinsic parameters $E_1$ of the imaging apparatus when taking the first radiographic image and the matrix of the extrinsic parameters $E_2$ of the imaging apparatus when taking the second radiographic image.

According to a first alternative embodiment of the method, the extrinsic parameters $E_2$ are estimated using the intrinsic parameters $I_1$ of the imaging apparatus in its first position, by minimizing the following criterion:

$$E_2 = \operatorname{argmin}\left(\sum_i \operatorname{dist}\left(\begin{pmatrix} \hat{x}^i \\ \hat{y}^i \end{pmatrix} - \begin{pmatrix} X_2^i \\ Y_2^i \end{pmatrix}\right)\right)$$

in which $$\begin{pmatrix} \hat{X}^i \\ \hat{Y}^i \end{pmatrix} = I * E_2 \begin{pmatrix} X_{marker} \\ Y_{marker} \\ Z_{marker} \end{pmatrix}$$

are the three-dimensional positions projected into the image by the projection matrix $I*E_2$, and $$\begin{pmatrix} X_2^i \\ Y_2^i \end{pmatrix}$$

are the two-dimensional positions of the markers observed in the second radiographic image. After having estimated the extrinsic parameters $E_2$, the movement M of the markers 14 i.e., the patient's movement M is extracted from the first equation.

The matrix of the intrinsic parameters $I_1$ of the imaging apparatus 1 when taking the first radiographic image is determined according to a so-called multi-image calibration method by placing a 3D phantom of known geometry between the radiation source 3 and the image receiver 2, then by taking n images of the 3D phantom in the determined fixed position of the imaging apparatus 1, where n is a positive integer of the order of 30, the 3D phantom being moved in rotation and/or translation between two successive images. The 3D phantom includes radio-opaque elements and may, for example, have a helical shaped as described in U.S. Pat. No. 5,442,674.

Thus, in order to determine the intrinsic parameters of the imaging apparatus in a determined fixed position, n images are acquired then the n projection matrices corresponding to the n images are calculated. The imaging apparatus 1 remains fixed during the acquisition of the n radiographic images, the intrinsic parameters are identical for all the images. Furthermore, since the 3D phantom is moved during the acquisition of the n images, the intrinsic parameters are different for each of the n images. It is then expedient to minimize an error function based on the projection of the errors calculated with n images, corresponding to the determined fixed position of the imaging apparatus 1 according to the equation E=argmin $(f(u_0, v_0, \alpha, R_1, T_1, R_2, T_2, \ldots, R_n, T_n))$ in which uo, vo and $\alpha$ are the three intrinsic parameters of the imaging apparatus 1 and $R_i$ and $T_i$ are the extrinsic parameters for image number i, in order to determine the intrinsic parameters of the imaging apparatus in its determined fixed position.

The error function can be written in the form:

$$f = \sum_{i=1}^{n} \sum_{j=1}^{} dist\left( \begin{pmatrix} \hat{X}^j \\ \hat{Y}^j \end{pmatrix} - \begin{pmatrix} X_2^j \\ Y_2^j \end{pmatrix} \right)$$

with $$\begin{pmatrix} X_2^j \\ Y_2^j \end{pmatrix}$$

being the two-dimensional positions of the markers observed in image number i, and the relation $$\begin{pmatrix} \hat{X}^j \\ \hat{Y}^j \end{pmatrix} = M_i \begin{pmatrix} X_{marker} \\ Y_{marker} \\ Z_{marker} \end{pmatrix}$$

in which $$\begin{pmatrix} X_{marker} \\ Y_{marker} \\ Z_{marker} \end{pmatrix}$$

are the three-dimensional positions projected into the image by the projection matrix $M_i$, and $$M_i = \begin{bmatrix} f & 0 & u_0 \\ 0 & f & v_0 \\ 0 & 0 & 1 \end{bmatrix} \begin{bmatrix} R_i & T_i \end{bmatrix}$$

is the projection matrix for image number i.

Figure 4:
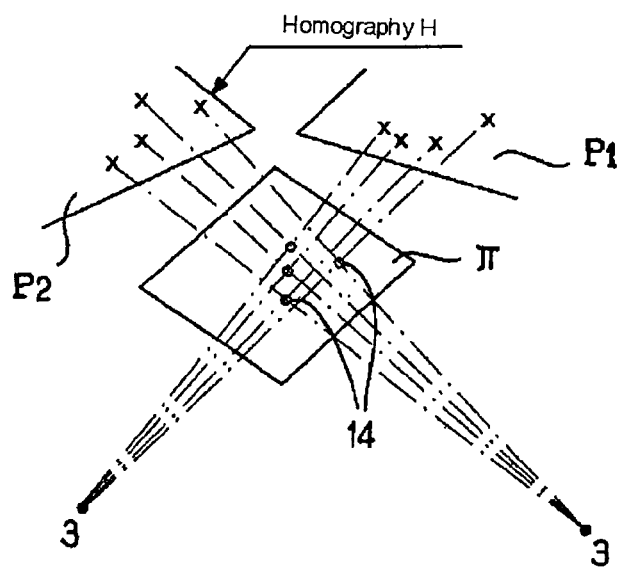
FIG. 4 is a schematic perspective view of the movement of the projections of the markers on the image receiver and of a radiation source according to a homography induced by the plane of the markers constituting a fixed reference frame.

According to a second alternative embodiment of the method, the matrix of the extrinsic parameters $E_2$ of the imaging apparatus when taking the second radiographic image is determined by calculating the planar homography H, i.e., the homography with respect to a plane $\pi$, between the first radiographic image of the markers 14 forming a plane $P_1$ and the second radiographic image of the markers 14 forming a second plane $P_2$, as schematically represented in FIG. 4. According to this homography H, the radiation source 2 moves when considering the fixed reference frame of the markers 14. Since the markers 14 extend in the same plane $\pi$, a planar homography H can thus be assigned between the plane $P_1$ of the first radiographic image and the plane $P_2$ of the second radiographic image; which can be written in the form $X2 \propto HX_1$ for all the markers 14 of the plane $\pi$, in which $\propto$ describes an equality involving a multiplicative factor.

Considering L, the three-dimensional movement between the three-dimensional coordinate system and the coordinate system in which the equation of the plane $\pi$ is y=0, we have the following for all the markers 14 of the plane $\pi$: $X_1 = <P_iL>*(x\ z\ 1)^t$ in which $<A>$ describes the matrix A without its second column. $<P_iL>$ is invertible unless the plane $\pi$ passes through the origin of the radiation source 3. It follows from the previous two equations that $<P_2L> \propto H<P_1L>$. The suppression of the second column of the matrix $P_2$ does not prevent the complete three-dimensional movement M of the markers 14 from being found. In view of the preceding equation, we know $<P_2L>$ and, since I is equal to $I_1$ and $I_2$ as seen above, we obtain the following equation: $I^{-1}H<P_1L> \propto [r_1\ r_3\ t]$ in which $r_1$ and $r_2$ are orthogonal vectors. The second column of the movement of the markers is simply given by $r_2=r_3 \times r_1$. This orthogonality condition is never perfectly satisfied in practice, and a renormalization should preferably be applied. It is then possible to calculate $E_2$ and M from the following to equations:

$$E_2 = [r_1 r_2 r_3 t] * L^{-1} \text{ and } M = E_1^{-1} * E_2.$$

It will be noted that one or other of the methods described above can be used to estimate the three-dimensional movement of the markers 14, the choice of method depending on the distribution of the markers 14 in the image.

Figure 5:
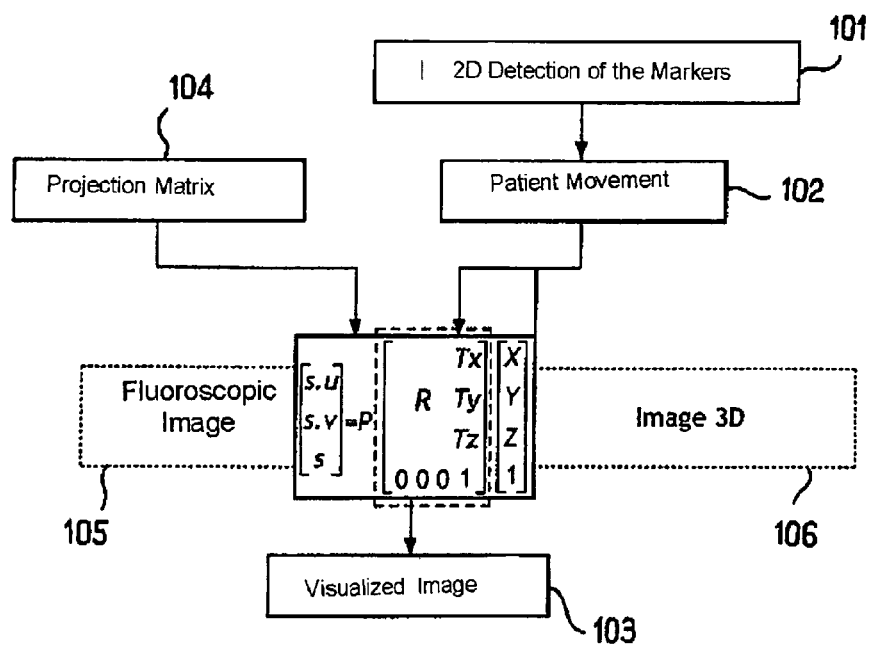
FIG. 5 is a schematic representation of a method for generating a radiographic image.

The method for determining the three-dimensional movement of a patient positioned on a table 12 between a radiation source 3 and an image receiver 2 of an imaging apparatus 1 is employed for adjusting the projection of a three-dimensionally reconstructed image of the patient's body onto radiographic images, or for repositioning two-dimensional radiographic image information in a three-dimensionally reconstructed image, which are displayed on the means for visualization 10 in order to assist the guiding of an object in an organ of the patient. Referring to FIG. 5, the 2D detection 101 of the radio-opaque markers makes it possible to deduce the patient's movement M 102. A computer program recorded in the means for operating 8 of the imaging apparatus 1 constructs a visualized image 103 by means of a projection matrix 104 on the basis of the patient's movement M 102, a radiographic image 105 and a three-dimensional image 106 of an organ of the patient, the visualized image 103 being the projection of a three-dimensional image of the patient's body onto radiographic images, or vice versa.

It is apparent that the markers 14 may be placed directly on the patient's body, at least three markers 14 forming a plane being desirable.

An embodiment of the method comprises: placing at least three radio-opaque markers on the body of the object, the markers constituting a fixed reference frame; taking at least one first radiographic image of the object for a first determined fixed position of the imaging apparatus in the reference frame of the markers; taking at least one second radiographic image of the object for a second determined fixed position of the imaging apparatus in the reference frame of the markers; determining the matrix of the three-dimensional movement of the object with respect to the means for providing a radiation source of the imaging apparatus on the basis of the two-dimensional movements of the markers in the radiographic images, the means for providing a radiation source then constituting a fixed reference frame.

In order to determine the patient's three-dimensional movement matrix with respect to the radiation source of the imaging apparatus on the basis of the two-dimensional movements of the markers in the radiographic images: the matrix of the intrinsic parameters of the imaging device is determined; the matrix of the extrinsic parameters of the imaging apparatus in the second position is determined as a function of the matrix of the intrinsic parameters of the imaging apparatus; the inverse matrix of the extrinsic parameters of the imaging apparatus in its first position is determined; the matrix corresponding to the three-dimensional movement of the object is determined as a function of the inverse matrix of the extrinsic parameters of the imaging apparatus in its first position in the fixed reference frame of the markers and the matrix of the extrinsic parameters of the imaging apparatus in its second position in the fixed reference frame of the markers.

According to the first alternative embodiment of the method, the matrix of the extrinsic parameters of the imaging apparatus when taking the second radiographic apparatus is determined as a function of the matrix of the intrinsic parameters of the imaging apparatus when taking the first radiographic image in the fixed reference frame of the markers.

According to the second alternative embodiment of the method, the matrix of the extrinsic parameters of the imaging apparatus when taking the second radiographic image is determined by calculating the planar homography H between the first radiographic image of the markers and the second radiographic image of the markers, the markers forming a fixed reference frame.

The markers can be either placed directly on the patient's body or are secured to a support placed on the patient's body.

The matrix and the inverse matrix of the extrinsic parameters of the imaging apparatus in its first position are determined on the basis of the matrix of the intrinsic parameters of the imaging apparatus.

The following steps can be used to determine the intrinsic parameters of the imaging device: a 3D phantom is placed between the radiation source and the image receiver; a plurality of images of the 3D phantom are acquired in the determined fixed position of the imaging apparatus; the 3D phantom being moved in rotation and/or translation between two successive images; and the intrinsic parameters of the imaging apparatus in its fixed position are calculated by performing a calibration on the basis of the images of the 3D phantom.

The method for determining the three-dimensional movement of an object positioned on a means for support between a radiation source and an image receiver of an imaging apparatus provides for adjusting the projection of a three-dimensionally reconstructed image of the object's body onto radiographic images, or in repositioning two-dimensional radiographic image information in three-dimensionally reconstructed images displayed on the means for visualization in order to assist the guiding of an object in or into an organ of the patient.

In addition, while an embodiment of the invention has been described with reference to exemplary embodiments, it will be understood by those skilled in the art that various changes may be made in the function and/or way and/or result and equivalents may be substituted for elements thereof without departing from the scope and extent of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. or steps do not denote any order or importance, but rather the terms first, second, etc. or steps are used to distinguish one element or feature from another. Furthermore, the use of the terms a, an, etc. do not denote a limitation of quantity, but rather denote the presence of at least one of the referenced element or feature.

What is claimed is:

1. A method for determining a three-dimensional movement of an object positioned on a table between an X-ray source and a digital image receiver in an imaging apparatus, wherein a plurality of radio-opaque markers are positioned on the object, the markers constituting a fixed reference frame and being within a single plane, the method comprising:

taking, with the X-ray source, at least one first radiographic image of the markers for a first determined fixed position of the imaging apparatus in the fixed reference frame of the markers, the at least one first radiographic image of the markers forming a first plane ($P_1$);

taking, with the X-ray source, at least one second radiographic image of the markers for a second determined fixed position of the imaging apparatus in the fixed reference frame of the markers, wherein the imaging apparatus has moved with respect to the first determined fixed position in the fixed reference frame of the markers, the at least one second radiographic image of the markers forming a second plane ($P_2$);

calculating, with respect to the fixed reference frame of the markers, a planar homography with respect to a third plane between the first plane ($P_1$) and the second plane ($P_2$);

determining a matrix ($E_2$) of extrinsic parameters of the imaging apparatus in the second determined fixed position by the calculating of the planar homography between the first plane ($P_1$) and the second plane ($P_2$);

determining an inverse matrix ($E_1^{-1}$) of extrinsic parameters of the imaging apparatus in the first determined fixed position; and determining a matrix of the three-dimensional movement of the object with respect to the X-ray source of the imaging apparatus as a function of the inverse matrix ($E_1^{-1}$) of the extrinsic parameters of the imaging apparatus in the first determined fixed position and the matrix ($E_2$) of the extrinsic parameters of the imaging apparatus in the second determined fixed position.

2. The method according to claim 1, further comprising: determining a matrix ($I_1$) of the intrinsic parameters of the imaging apparatus.

3. The method according to claim 2, wherein a 3D phantom is positioned between the X-ray source and the digital image receiver, and wherein determining the matrix of the intrinsic parameters of the imaging apparatus comprises:

acquiring a plurality of images of the 3D phantom in a determined fixed position of the imaging apparatus, the 3D phantom being moved in rotation and/or translation between two successive images; and calculating the matrix of the intrinsic parameters of the imaging apparatus in the determined fixed position by performing a calibration on the basis of the images of the 3D phantom.

4. The method according to claim 1, further comprising: adjusting a projection of a three-dimensionally reconstructed image of the body of the object onto two-dimensional radiographic images; and displaying the image.

5. The method according to claim 1, further comprising: repositioning two-dimensional radiographic image information in a three-dimensionally reconstructed image; and displaying the image.

6. The method according to claim 1, wherein the plurality of markers is at least three.

* * * * *